(12) United States Patent
Chen et al.

(10) Patent No.: US 12,037,352 B2
(45) Date of Patent: *Jul. 16, 2024

(54) PERFLUOROPOLYETHER COMPOUND CONTAINING CARBOXYL GROUP

(71) Applicant: GUANGZHOU UR MATERIALS TECHNOLOGY CO., LTD., Guangdong (CN)

(72) Inventors: Yi-Jing Chen, Guangdong (CN); Qi-Guan Wang, Guangdong (CN); Gong-Zhou Chen, Guangdong (CN)

(73) Assignee: GUANGZHOU UR MATERIALS TECHNOLOGY CO., LTD., Guangdong (CN)

( * ) Notice: Subject to any disclaimer, the term of this patent is extended or adjusted under 35 U.S.C. 154(b) by 781 days.

This patent is subject to a terminal disclaimer.

(21) Appl. No.: 17/055,964

(22) PCT Filed: May 7, 2019

(86) PCT No.: PCT/CN2019/085891
§ 371 (c)(1),
(2) Date: Nov. 16, 2020

(87) PCT Pub. No.: WO2019/218902
PCT Pub. Date: Nov. 21, 2019

(65) Prior Publication Data
US 2021/0206917 A1    Jul. 8, 2021

(30) Foreign Application Priority Data

May 16, 2018  (CN) .......................... 201810468845.1

(51) Int. Cl.
| | | |
|---|---|---|
| C03C 17/30 | (2006.01) | |
| C03C 17/42 | (2006.01) | |
| C07F 7/08 | (2006.01) | |
| C07F 7/18 | (2006.01) | |
| C08G 65/332 | (2006.01) | |
| C08G 65/336 | (2006.01) | |
| C09D 5/16 | (2006.01) | |
| C09D 171/02 | (2006.01) | |

(52) U.S. Cl.
CPC ............ $C07F\ 7/1804$ (2013.01); $C03C\ 17/30$ (2013.01); $C03C\ 17/42$ (2013.01); $C07F\ 7/081$ (2013.01); $C07F\ 7/1876$ (2013.01); $C08G\ 65/3322$ (2013.01); $C08G\ 65/336$ (2013.01); $C09D\ 5/1662$ (2013.01); $C09D\ 171/02$ (2013.01); $C03C\ 2217/76$ (2013.01); $C03C\ 2217/78$ (2013.01); $C03C\ 2218/151$ (2013.01); $C08G\ 2650/48$ (2013.01)

(58) Field of Classification Search
USPC ........................................... 528/401
See application file for complete search history.

(56) References Cited

FOREIGN PATENT DOCUMENTS

| | | | | |
|---|---|---|---|---|
| CN | 104220485 A | 12/2014 | | |
| CN | 104826361 A | 8/2015 | | |
| CN | 105111351 A | 12/2015 | | |
| CN | 106661436 A | * 5/2017 | ............... | C07F 7/18 |
| CN | 106661436 A | 5/2017 | | |
| CN | 109071793 A | 12/2018 | | |
| WO | 03010128 A2 | 2/2003 | | |
| WO | 2018079525 A1 | 5/2018 | | |
| WO | WO-2018079525 A1 | * 5/2018 | ............. | B32B 27/30 |

OTHER PUBLICATIONS

CN 106661436 A Machine Translation (Year: 2017).*
International Search Report and Written Opinion, dated Aug. 20, 2019, for International Patent Application No. PCT/CN2019/085891. (11 pages).

* cited by examiner

Primary Examiner — Terressa Boykin
(74) Attorney, Agent, or Firm — Seed IP Law Group LLP

(57) ABSTRACT

Disclosed herein are carboxyl group containing perfluoropolyether compounds of formula (I): $Rf-X^1-X^2$ (I), wherein the groups Rf, $X^1$ and $X^2$ are defined herein. Also disclosed are methods of preparing and using perfluoropolyether compounds.

16 Claims, No Drawings

PERFLUOROPOLYETHER COMPOUND CONTAINING CARBOXYL GROUP

CROSS REFERENCE TO RELATED APPLICATIONS

This application is a National Stage of PCT/CN2019/085891 filed on May 7, 2019, which claims benefit of priority from Chinese Application No. 201810468845.1, filed on May 16, 2018, the entire contents of which are incorporated herein by reference.

FIELD OF INVENTION

The present invention relates to perfluoropolyether compound containing a carboxyl group, and a preparation method for the perfluoropolyether compound containing a carboxyl group.

BACKGROUND OF THE INVENTION

Perfluoropolyether group-containing silane compounds are known in the prior art. They can form a hydrophobic, oleophobic, antifouling, low friction coefficient and durable film on the surface of a substrate due to the low surface energy characteristic of the perfluoropolyether group within their molecules, and a chemical bond for binding formed by a dehydration condensation reaction of the siloxane group within the molecules on the surface of the substrate. A film layer having protective function can be formed by uniformly dispersing a surface treatment agent comprising the compound on a substrate in a way of spraying or vapor deposition and then heating and curing it. Since the film layer is only a few nanometers thick and transparent, it will not affect the appearance and light transmittance of the substrate surface.

However, due to the influence of the perfluoropolyether chain, generally it is not easy for the perfluoropolyether-based compound to further perform a reaction to synthesize a perfluoropolyether-based silane compound.

Shin-Etsu and Daikin companies from Japan have conducted more intensive research in this field, applying the material to the protection of camera lenses, and extending the use to touch glass of electronic products, which satisfies the anti-fouling, anti-fingerprint, scratch resistance, high slip, wear resistance and durability requirements for the screens of mobile phones and tablet computers.

CN 104769009 B discloses a perfluoropolyether group containing silane compound, represented by the following representative structural formula:

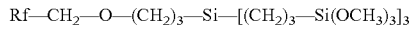

Its synthesis method is as follows:

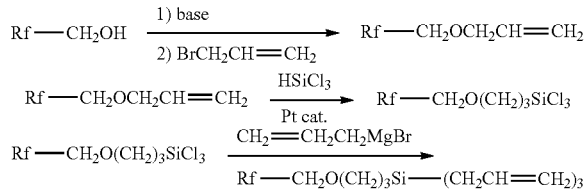

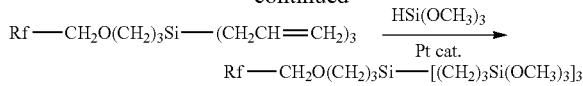

However, the above-mentioned synthesis method requires harsh conditions (for example, strict anhydrous operation is required), and uses very sensitive chemicals such as $HSiCl_3$, Grignard reagent and the like. $HSiCl_3$ is very corrosive and has high equipment requirements; Grignard reagents and Pt catalysts are expensive, resulting in abnormally high production costs.

US 2015/0191629 A1 discloses another perfluoropolyether-based silane compound, represented by the following typical structure:

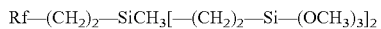

Its synthesis method is as follows:

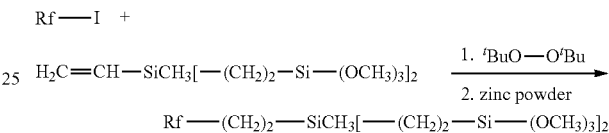

However, Rf—I is a non-commercially available product, which needs to be synthesized and converted first; and the silane coupling agent used is also a non-commercially available product, which requires a customized synthesis, so the cost is also high.

Therefore, there is a need to provide an intermediate raw material capable of easily reacting with a silane compound to prepare a perfluoropolyether-based silane compound as a surface treatment agent with excellent surface treatment performance, and a preparation method thereof.

SUMMARY

To solve the technical problem in the prior art, the present invention provides a carboxyl group containing perfluoropolyether compound. The carboxyl group containing perfluoropolyether compound as an intermediate material can be used for the convenient preparation of a perfluoropolyether group-containing silane compound.

According to one aspect of the present invention, a carboxyl group containing perfluoropolyether compound of formula (I) is provided:

wherein Rf represents $F—(CF_2)_m—(OC_4F_8)_p—(OC_3F_6)_q—(OC_2F_4)_r—(OCF_2)_s—OC(Z)F—(CF_2)_n—$, here, p, q, r and s are each independently an integer of 0 or more and 200 or less, the sum of p, q, r and s is at least 1, the occurrence order and number of the respective repeating units in parentheses with the subscript p, q, r or s are arbitrary in the formula; m and n are each independently an integer of 0 or more and 30 or less; Z is F or $CF_3$; $X^1$ represents a divalent organic group; and $X^2$ represents a COOH group.

In some preferred embodiments, Rf is the following formula (a) or (b):

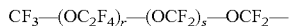 (a):

wherein the sum of r and s is an integer of 10 or more and 200 or less;

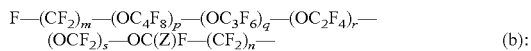
(b):

wherein m is an integer of 1 to 16, n is an integer of 0 to 2, r and s are each independently an integer of 1 or more and 200 or less, the sum of p, q, r and s is 10 or more and 200 or less, the occurrence order and number of the respective repeating units in parentheses with the subscript p, q, r or s are arbitrary in the formula.

In some preferred embodiments, $X^1$ is a group as follow:

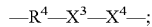

wherein $R^4$ is $C_{1-6}$ alkyl group, or a substituted $C_{1-6}$ alkyl group; $X^3$ is selected from a group consisting of —O—, —S—, an o-, m- or p-phenylene group, an o-, m- or p-benzylidene group, —C(O)O—, —CONR$^5$—, —O—CONR$^5$—, —NR$^5$—, —Si(R$^6$)$_2$—, —(Si(R$^6$)$_2$O)$_f$—Si(R$^6$)$_2$— and —(CH$_2$)$_g$—; $R^5$ represents, each independently at each occurrence, a hydrogen atom, a phenyl group or $C_{1-6}$ alkyl group; $R^6$ is $C_{1-6}$ alkyl group, or a substituted $C_{1-6}$ alkyl group; f is, each independently at each occurrence, an integer of 1-100; g is, each independently at each occurrence, an integer of 1-20; $X^4$ is a divalent group.

In some preferred embodiments, $X^4$ is a group as represented by —(R$^7$)$_a$—(X$^5$)$_b$—R$^8$—, wherein: $R^7$ represents —(CH$_2$)$_c$—, an o-, m- or p-phenylene group, or an o-, m- or p-benzylidene group, $R^8$ represents —(CH$_2$)$_d$—, an o-, m- or p-phenylene group, or an o-, m- or p-benzylidene group, $X^5$ represents —(X$^6$)$_e$—, $X^6$ represents, each independently at each occurrence, a group selected from —O—, —S—, an o-, m- or p-phenylene group, an o-, m- or p-benzylidene group, —C(O)O—, —CONR$^5$—, —O—CONR$^5$—, —NR$^5$—, —Si(R$^6$)$_2$—, —(Si(R$^6$)$_2$O)$_f$—Si(R$^6$)$_2$— and —(CH$_2$)$_g$—; $R^5$ represents, each independently at each occurrence, a hydrogen atom, a phenyl group or $C_{1-6}$ alkyl group; $R^6$ represents, each independently at each occurrence, a phenyl group or $C_{1-6}$ alkyl group; f is, each independently at each occurrence, an integer of 1-100; g is, each independently at each occurrence, an integer of 1-20; a is 0 or 1; b is 0 or 1; c is an integer of 1-20; d is an integer of 1-20; e is an integer of 1-10.

Further, as a result of studying, the inventors of the present invention have connected a perfluoropolyether group to the carboxyl group via a space group, which makes the subsequent further reaction of the carboxyl group be easy, thus the purpose of the present invention is achieved.

According to a more preferred embodiment of the present invention, a carboxyl group containing perfluoropolyether compound has the following general chemical formula (II), Rf—CH$_2$—O—X—COOH (II)

wherein, Rf is

p, q and r are each independently an integer of 1 or more and 200 or less, the sum of p, q and r is at least 1, the occurrence order of the respective repeating units in parentheses with the subscript p, q or r is arbitrary in the formula, m is an integer of 1 to 16, n is 0 or 1, Z represents a fluorine atom or a trifluoromethyl; or Rf represents CF$_3$(OC$_2$F$_4$)$_p$(OCF$_2$)$_q$OCF$_2$, wherein p and q are each independently an integer of 0 or more and 200 or less, the sum of p and q is at least 1, the occurrence order of the respective repeating units in parentheses with the subscript p or q is arbitrary in the formula; preferably, the sum of p and q is 20-100;

X represents a divalent organic group.

According to some preferred embodiments of the present invention, X in the aforementioned compound of formula (II) represents $C_{1-6}$ alkylene group, —CH$_2$C$_6$H$_4$—, or —CH$_2$C$_6$H$_4$— with a substituent on the benzene ring.

According to some preferred embodiments of the present invention, X in the aforementioned compound of formula (II) is selected from a group as follows: —CH$_2$—, —CH(CH$_3$)—, —(CH$_2$)$_2$—, —(CH$_2$)$_3$—, —(CH$_2$)$_4$—, —(CH$_2$)$_6$—, —CH$_2$C$_6$H$_4$—.

According to some preferred embodiments of the present invention, the aforementioned compound of formula (II) has a number average molecular weight of 500-10,000.

According to some preferred embodiments of the present invention, a preparation method for the aforementioned perfluoropolyether based compound represented by formula (II) comprises:

Step 1: first reacting a compound of the formula Rf—CH$_2$OH with a base in the presence of a solvent, then reacting with a compound of the formula L-X-G to perform a nucleophilic substitution, thus obtaining a perfluoropolyether compound of formula Rf—CH$_2$—O—X-G,

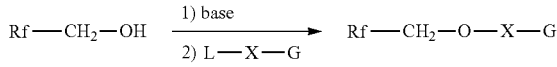

wherein, L represents a leaving group or atom where a nucleophilic substitution reaction can occur; G represents a group that can be hydrolyzed into a carboxylic acid; X represents a divalent organic group, preferably is $C_{1-6}$ alkylene group, —CH$_2$C$_6$H$_4$—, or —CH$_2$C$_6$H$_4$— with a substituent on the benzene ring;

Step 2: hydrolyzing the compound of formula Rf—CH$_2$—O—X-G to obtain a perfluoropolyether compound of formula Rf—CH$_2$—O—X—COOH,

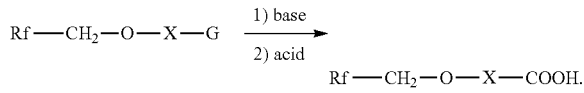

According to some preferred embodiments of the present invention, the base in above step 1 is selected from inorganic base or organic base; inorganic base is preferably selected from at least one of LiOH, NaOH, KOH, K$_2$CO$_3$, Na$_2$CO$_3$, Cs$_2$CO$_3$, NaH, t-BuOK; organic base is preferably selected from at least one of DIPEA, DBU, or 1,1,3,3-tetramethylguanidine.

According to some preferred embodiments of the present invention, in the compound of the aforementioned formula L-X-G, L is a chlorine atom, a bromine atom, or an iodine atom.

According to some preferred embodiments of the present invention, in the compound of the aforementioned formula L-X-G; G is an ester group, a nitrile group, an amide group, or a substituted amide group.

According to some preferred embodiments of the present invention, in the compound of the aforementioned formula L-X-G, X is selected from a group as follows: —CH$_2$—, —CH(CH$_3$)—, —(CH$_2$)$_2$—, —(CH$_2$)$_3$—, —(CH$_2$)$_4$—, —(CH$_2$)$_6$—, —CH$_2$C$_6$H$_4$—.

According to some preferred embodiments of the present invention, the solvent in above step (1) is fluorinated solvent, preferably hydrofluoroether or fluorinated hydrocarbon.

According to some preferred embodiments of the present invention, the base in above step 2 is selected from at least one of sodium hydroxide, potassium hydroxide, lithium hydroxide and cesium hydroxide.

According to some preferred embodiments of the present invention, the acid in above step 2 is selected from inorganic acids. Further, the acid is selected from at least one of hydrochloric acid, sulfuric acid, or nitric acid.

According to a preferred embodiment of the present invention, the present invention further provides a use of the perfluoropolyether-based compound of formula (II) for the manufacture of a perfluoropolyether based silane compound.

According to a preferred embodiment of the present invention, the present invention further provides a method for preparing a perfluoropolyether group containing silane compound, wherein the carboxyl group containing perfluoropolyether compound of formula (II) is an intermediate. According to a preferred embodiment of the present invention, the present invention further provides a use of the perfluoropolyether group containing silane compound produced by the method for the application in metal anti-corrosion, hydrophobic and oleophobic, lubricants, mold release agents, biosensing, electronic equipment interface controls.

DETAILED DESCRIPTION OF THE INVENTION

To make the purposes, technical solutions and advantages of the present invention clearer, the technical solutions in the Examples of the present invention will be clearly and completely described below. It is obvious that the described examples are one portion of the examples of the present invention, but not all the examples. Based on the examples of the present invention, all the other examples obtained without creative labor by one of ordinary skill in the art fall into the scope protected by the present invention.

Each specific example of the present application is sufficiently described below in detail, so that one of ordinary skill in the art having related knowledge and techniques can carry out the technical solutions of the present application. It should be understood that other examples can also be used, or that modifications or changes can be made to the examples of the present application.

According to some preferred embodiments of the present invention, a perfluoropolyether-based compound is characterized by having the following general chemical formula (II), Rf—CH$_2$—O—X—COOH    (II)

wherein, Rf is

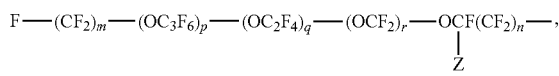

p, q and r are each independently an integer of 1 or more and 200 or less, the sum of p, q and r is at least 1, the occurrence order of the respective repeating units in parentheses with the subscript p, q or r is arbitrary in the formula, m is an integer of 1 to 16, n is 0 or 1, Z represents a fluorine atom or a trifluoromethyl;

or

Rf represents CF$_3$(OC$_2$F$_4$)$_p$(OCF$_2$)$_q$OCF$_2$, wherein p and q are each independently an integer of 0 or more and 200 or less, the sum of p and q is at least 1, the occurrence order of the respective repeating units in parentheses with the subscript p or q is arbitrary in the formula; preferably, the sum of p and q is 20-100;

X represents a divalent organic group.

According to some preferred embodiments of the present invention, X in the aforementioned compound of formula (II) represents C$_{1-6}$ alkylene group, —CH$_2$C$_6$H$_4$—, or —CH$_2$C$_6$H$_4$— with a substituent on the benzene ring.

According to some preferred embodiments of the present invention, X in the aforementioned compound of formula (II) is selected from a group as follows: —CH$_2$—, —CH(CH$_3$)—, —(CH$_2$)$_2$—, —(CH$_2$)$_3$—, —(CH$_2$)$_4$—, —(CH$_2$)$_6$—, —CH$_2$C$_6$H$_4$—.

According to some preferred embodiments of the present invention, the aforementioned compound of formula (II) has a number average molecular weight of 500-10,000.

According to some preferred embodiments of the present invention, the preparation process for Rf—CH$_2$—O—X—COOH comprises:

Step 1: first reacting a compound of the formula Rf—CH$_2$OH with a base in the presence of a solvent, then reacting with a compound of the formula L-X-G to perform a nucleophilic substitution, thus obtaining a perfluoropolyether compound of formula Rf—CH$_2$—O—X-G,

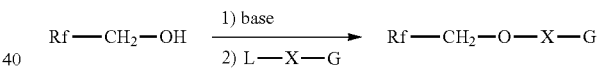

wherein, L represents a leaving group where a nucleophilic substitution reaction can occur; G represents a group that can be hydrolyzed into a carboxyl; X represents a divalent organic group;

Step 2: hydrolyzing the compound of formula Rf—CH$_2$—O—X-G to obtain a carboxyl group containing perfluoropolyether compound of formula Rf—CH$_2$—O—X—COOH,

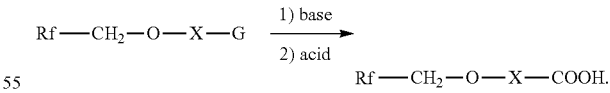

According to some preferred embodiments, the base in step 1 is selected from inorganic base or organic base; inorganic base is preferably selected from at least one of LiOH, NaOH, KOH, K$_2$CO$_3$, Na$_2$CO$_3$, Cs$_2$CO$_3$, NaH, t-BuOK; organic base is preferably selected from at least one of DIPEA, DBU, 1,1,3,3-tetramethylguanidine. More preferably, the base is selected from at least one of sodium hydroxide, potassium hydroxide, lithium hydroxide, cesium hydroxide, sodium carbonate, potassium carbonate and cesium carbonate.

According to some preferred embodiments, in the compound of the aforementioned formula L-X-G, L is a chlorine atom, a bromine atom, or an iodine atom.

According to some preferred embodiments, in the compound of the aforementioned formula L-X-G, X is $C_{1-20}$ alkylene group, more preferably $C_{1-6}$ alkylene group, —$CH_2C_6H_4$— or —$CH_2C_6H_4$— with a substituent on the benzene ring.

According to some preferred embodiments, in the compound of the formula L-X-G; G is an ester group, a nitrile group, an amide group, or a substituted amide group. Further, the examples of the ester can be methyl ester, ethyl ester, propyl ester, isopropyl ester, phenyl ester, benzyl ester, etc. The examples of the amides can be N-substituted amide or N, N-disubstituted amide.

According to some preferred embodiments, the examples of the compounds of the formula L-X-G include but are not limited to:

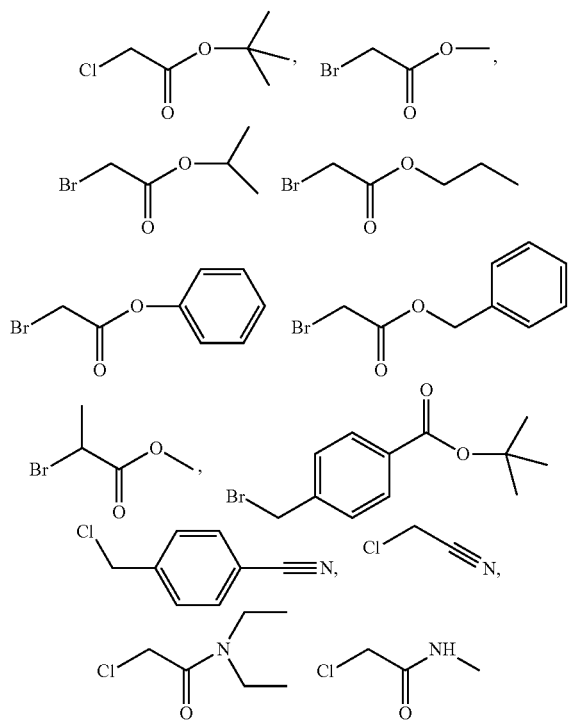

According to some preferred embodiments, the base in aforementioned step 2 is selected from at least one of sodium hydroxide, potassium hydroxide, lithium hydroxide, cesium hydroxide.

According to some preferred embodiments, the acid in aforementioned step 2 is selected from inorganic acids, and the examples of the inorganic acids can include hydrochloric acid, sulfuric acid, phosphoric acid, or nitric acid.

According to a more preferred embodiment of the present invention, the method for preparing a carboxyl group containing perfluoropolyether-based compound comprises the following steps:

Step 1: first reacting a compound of the formula Rf—$CH_2OH$ with potassium hydroxide at room temperature in the presence of a solvent, then reacting with a compound of the formula $BrCH_2COOC_4H_9$ at normal or heated (preferably 25-75° C.) temperature to perform a nucleophilic substitution, thus obtaining an esteryl containing perfluoropolyether compound of formula Rf—$CH_2$—$OCH_2COOC_4H_9$,

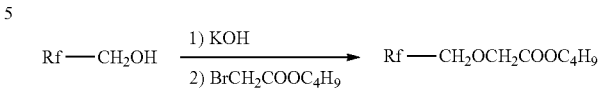

Rf represents $CF_3(OCF_2CF_2)_p(OCF_2)_qOCF_2$—, p+q is 35-85, which has a number average molecule weight of 3000-8000;

Step 2: reacting the esteryl perfluoropolyether compound of formula Rf—$CH_2$—$OCH_2COOC_4H_9$ with a base to perform hydrolyzation, adding hydrochloric acid to adjust acidity, separating and obtaining a carboxyl group containing perfluoropolyether compound of formula Rf—$CH_2$—O—$CH_2COOH$,

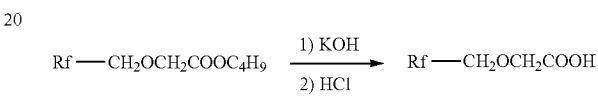

In the preparation process of the present invention, there is no limitation to the solvent used, as long as it is a solvent that can dissolve perfluoropolyether alcohol, an esteryl perfluoropolyether compound, carboxyl perfluoropolyether compound and the like under the condition of normal temperature or heating. It is preferably a fluorinated solvent, such as hydrofluoroether, fluorinated hydrocarbon, etc., and more preferably nonafluorobutyl ethyl ether, nonafluorobutyl methyl ether, perfluorohexane, m-trifluorotoluene, etc.

The preparation process of the present invention can be performed under the condition of normal temperature or heating. Preferably, the nucleophilic substitution reaction of perfluoropolyether alcohol in step 1 can be conducted at 25-75° C., and preferably, the acyl halogenation reaction in step 3 can be conducted at 25-50° C.

As described above, in the present invention, an esteryl perfluoropolyether compound of formula Rf—$CH_2$—O—X-G is obtained by reacting a compound of formula Rf—$CH_2OH$ with a compound of the formula L-X-G to perform a nucleophilic substitution, wherein, L represents a leaving group where a nucleophilic substitution reaction can occur, G represents a group that can be hydrolyzed to carboxyl, X represents a bivalent organic group; and then a completely new intermediate, i.e. carboxyl perfluoropolyether compound of formula Rf—$CH_2$—O—X—COOH, is obtained by hydrolyzation. Since the perfluoropolyetheryl is linked to the carboxyl group through the space group X, the subsequent further reactions of the carboxyl group become easy to be performed, such as a reaction with the aminosilane coupling agent can obtain the perfluoropolyether group containing aminosilane compound in the patent application CN 201880000606.1 filed by the present applicant. As a commercialized raw material, Rf—$CH_2OH$ is easily available, and easy to perform a nucleophilic substitution reaction with the compound of formula L-X-G, and then hydrolysis to prepare an intermediate of formula Rf—$CH_2$—O—X—COOH. The intermediate of formula Rf—$CH_2$—O—X—COOH can be used as a starting material to readily perform further follow-up reactions of a carboxyl group, thereby a variety of derivative compounds containing perfluoropolyetheryl and carbonyl groups are obtained. For example, the carboxyl group can react with an acyl halogenation agent to produce an acylhalide; condense with a carboxylic acid to produce an anhydride, condense with an alcohol to produce an ester, react with an amine to produce an amide, and a primary amide can be dehydrated to be prepared into a nitrile.

According to a preferred embodiment of the present invention, Rf—$CH_2$—O—$CH_2$COOH can be used to prepare a perfluoropolyether silane compound of the formula Rf—$CH_2$—O—$CH_2$CON[$CH_2CH_2CH_2$Si($OCH_3$)$_3$]$_2$ for surface treatment according to the following procedure: a carboxyl perfluoropolyether compound of the formula Rf—$CH_2$—O—$CH_2$COOH is reacted with oxalyl chloride at a temperature of 25-50° C., and then reacted with bis(trimethylsilylpropyl)amine at room temperature to obtain a perfluoropolyether silane compound of the formula Rf—$CH_2$—O—$CH_2$CON[$CH_2CH_2CH_2$Si($OCH_3$)$_3$]$_2$.

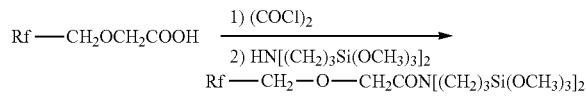

EXAMPLES

Synthesis Example 1

A terminal carboxyl group containing perfluoropolyether-based compound M2 is synthesized according to the following steps.

Step 1:
10 g perfluoropolyether modified alcohol (a number average molecule weight of 3500~4000, manufactured by SOLVAY company) with an average composition of $CF_3$($OCF_2CF_2$)$_p$($OCF_2$)$_q$$OCF_2CH_2$OH (the sum of p and q is 35-42), 15 mL 1,3-bis(trifluoromethyl) benzene, 5 mL ethylene glycol dimethyl ether, 2.6 g 50 wt % potassium hydroxide solution are added into a 100-mL three-neck round-bottom flask equipped with a stirrer, and stirred at room temperature for 3 hours. 3.8 mL tert-butyl bromoacetate, then 0.42 g tetrabutylammonium bromide are sequentially added into the reaction flask, and stirred at 50° C. for 5 hours. 9.6 g of a colorless, transparent product is obtained by extraction with water and decompression distillation, i.e., a terminal esteryl perfluoropolyether compound (M1): $CF_3$($OCF_2CF_2$)$_p$($OCF_2$)$_q$$OCF_2CH_2OCH_2COOC_4H_9$.

By identification with a nuclear magnetic resonance (NMR) spectrometer, the characteristic $^1$H chemical shifts of the newly-added structures are shown in the table below.

| Group structure | δ, ppm |
|---|---|
| $CH_2$— | 4.136 (s) |
| —$CF_2CH_2$— | 4.058~3.996 (q) |
| —$COOC_4H_9$ | 1.498(s) |

Step 2:
9.6 g esteryl perfluoropolyether compound (M1) obtained in step 1, 17 g 10 wt % potassium hydroxide solution are added into a 100-mL three-neck round-bottom flask equipped with a thermometer and a stirrer, stirred at 100° C. for 3 hours, and then reduced to room temperature. 10 mL tetrahydrofuran is added thereto, and after being adjusted to be acidic with 2N hydrochloric acid, 30 mL hydrofluoroether HFE-7200 (produced by 3M Company) is added and stirred. The non-fluorine phase (i.e., the upper solution) is removed, and the fluorine phase is washed 2 times with 2N hydrochloric acid, and finally 9.0 g of a colorless, transparent product is obtained by decompression distillation, i.e., a terminal carboxyl perfluoropolyether compound (M2): $CF_3$($OCF_2CF_2$)$_p$($OCF_2$)$_q$$OCF_2CH_2OCH_2$COOH.

By identification with a NMR spectrometer, the characteristic $^1$H chemical shifts of the newly-added structures are shown in the table below.

| Group structure | δ, ppm |
|---|---|
| —$OCH_2$— | 4.308 (s) |
| —$CF_2CH_2$— | 4.063~4.001 (g) |

By identification with a Fourier transform infrared spectrometer, the structural characteristic absorption peaks thereof are shown in the table below

| Group structure | λ, cm$^{-1}$ |
|---|---|
| —COOH | 2900~3100 (O—H stretch) |
| —COOH | 1739 (C=O stretch) |
| C—O/C—F | 1040~1335 (perfluoropolyether characteristic band) |

Synthesis Example 2

A terminal carboxyl group containing perfluoropolyether-based compound M4 is synthesized according to the following steps.

Step 1:
10 g perfluoropolyether modified alcohol (a number average molecule weight of 4500~5000, manufactured by SOLVAY company) with an average composition of $CF_3$($OCF_2CF_2$)$_p$($OCF_2$)$_q$$OCF_2CH_2$OH (the sum of p and q is 47~52), 15 mL 1,3-bis(trifluoromethyl) benzene, 5 mL ethylene glycol dimethyl ether, 2.0 g 50 wt % potassium hydroxide solution are added into a 100-mL three-neck round-bottom flask equipped with a stirrer, and stirred at room temperature for 3 hours. 3.2 mL tert-butyl bromoacetate, then 0.32 g tetrabutylammonium bromide are sequentially added to the reaction flask, and stirred at 50° C. for 5 hours. 9.6 g of a colorless, transparent product is obtained by extraction with water and decompression distillation, i.e. a terminal esteryl perfluoropolyether compound (M3): $CF_3$($OCF_2CF_2$)$_p$($OCF_2$)$OCF_2CH_2OCH_2COOC_4H_9$.

By identification with a NMR spectrometer, the characteristic $^1$H chemical shifts are shown in the table below.

| Group structure | δ, ppm |
|---|---|
| —$OCH_2$— | 4.140 (s) |
| —$CF_2CH_2$— | 4.065~4.003 (q) |
| —$COOC_4H_9$ | 1.501(s) |

Step 2:
9.6 g esteryl perfluoropolyether compound (M3) obtained in step 1, 17 g 10 wt % potassium hydroxide solution are added into a 100-mL three-neck round-bottom flask equipped with a thermometer and a stirrer, stirred at 100° C. for 10 hours, and reduced to room temperature. 10 mL tetrahydrofuran is added thereto, and after being adjusted to be acidic with 150% hydrochloric acid, 30 mL hydrofluoroether HFE-7200 (produced by 3M Company) is added and stirred. The non-fluorine phase (i.e., the upper solution) is removed, and the fluorine phase is washed twice with 2N hydrochloric acid, and finally the colorless transparent product 9.0 g is obtained by decompression distillation, i.e., a terminal carboxyl perfluoropolyether compound (M4): $CF_3(OCF_2CF_2)_p(OCF_2)OCF_2OCH_2COOH$.

By identification with a NMR spectrometer, the characteristic $^1H$ chemical shifts are shown in the table below.

| Group structure | δ, ppm |
|---|---|
| —OCH$_2$— | 4.310 (s) |
| —CF$_2$CH$_2$— | 4.069~3.998 (g) |

By identification with a Fourier transform infrared spectrometer, the structural characteristic absorption peaks thereof are shown in the table below

| Group structure | λ, cm$^{-1}$ |
|---|---|
| —COOH | 2900~3100 (O—H stretch) |
| —COOH | 1739 (C═O stretch) |
| C—O/C—F | 1040~1335 (perfluoropolyethercharacteristic band) |

Synthesis Example 3

A terminal carboxyl group containing perfluoropolyether-based compound M6 is synthesized according to the following steps.

Step 1:

3 g perfluoropolyether modified alcohol (a number average molecule weight of 3500~4000, manufactured by SOLVAY company) with an average composition of $CF_3(OCF_2CF_2)_p(OCF_2)_qOCF_2CH_2OH$ (the range of p+q is 35-42), 9 mL hydrofluoroether HFE-7200, and 3 mL t-BuOH are added into a 100-mL three-neck round-bottom flask equipped with a stirrer, to dissolve. Next, 0.45 g t-BuOK is added thereto and stirred at room temperature for 1.5 hours. 1.5 g $BrCH_2C_6H_4COOC_4H_9$, then 0.12 g tetrabutylammonium bromide are sequentially added to the reaction flask, and stirred at 50° C. for 1.5 hours. Extraction with water and then decompression distillation are performed to obtain a colorless transparent liquid (M5): $CF_3(OCF_2CF_2)_p(OCF_2)_qOCF_2CH_2OCH_2C_6H_4COOC_4H_9$.

Step 2:

The obtained colorless transparent liquid (M5) is added into a 100-mL three-neck round-bottom flask equipped with a thermometer and a stirrer, and 9 mL 20 wt % potassium hydroxide solution is added, and stirred at 115° C. for 5 hours. It is reduced to room temperature and after being adjusted to be acidic with 2N hydrochloric acid, distilled water and tetrahydrofuran are added for extraction. 2.63 g of a colorless transparent product is obtained by decompression distillation, i.e. a terminal carboxyl perfluoropolyether compound (M6): $CF_3(OCF_2CF_2)_p(OCF_2)_qOCF_2CH_2OCH_2C_6H_4COOH$.

By identification with a NMR spectrometer, the characteristic $^1H$ chemical shifts are shown in the table below

| Group structure | δ, ppm |
|---|---|
| —C$_6$H$_4$— | 8.105~8.090 (d), 7.576~7.563 (d) |
| —OCH$_2$— | 4.949 (s) |
| —CF$_2$CH$_2$— | 4.099~4.040 (m) |

By identification with a Fourier transform infrared spectrometer, the structural characteristic absorption peaks thereof are shown in the table below

| Group structure | λ, cm$^{-1}$ |
|---|---|
| —COOH | 2900~3100 (O—H stretch) |
| —COOH | 1702 (C═O stretch) |
| —C$_6$H$_4$— | 1617, 1580(C═C Skeletal) |
| C—O/C—F | 1040~1335 (perfluoropolyethercharacteristic band) |

Synthesis Example 4

A terminal carboxyl group containing perfluoropolyether-based compound M2 is synthesized according to the following steps.

1 g perfluoropolyether modified alcohol (a number average molecule weight of 3500~4000, manufactured by SOLVAY company) with an average composition of $CF_3(OCF_2CF_2)_p(OCF_2)_qOCF_2CH_2OH$ (the range of p+q is 35-42), 1.5 mL 1,3-bis(trifluoromethyl) benzene, and 0.5 mL ethylene glycol dimethyl ether are added into a 100-mL three-neck round-bottom flask equipped with a stirrer, and stirred at room temperature. Next, 0.09 g of sodium hydride is added and the generation of bubbles is observed. 0.199 g ClCH$_2$CN, then 0.044 g tetrabutylammonium bromide are sequentially added into the reaction flask, and stirred at 50° C. for 3 hours. 5 mL hydrofluoroether HFE-7200 is added. A bright yellow transparent solution is obtained by filtration through a filter membrane. By extraction with water and decompression distillation, a yellow-brown product (M7), $CF_3(OCF_2CF_2)_p(OCF_2)_qOCF_2CH_2OCH_2CN$, is obtained. Next, 3 g 20 wt % potassium hydroxide solution is added and reflux hydrolysis is performed at 115° C. By acidifiation and purification, 0.74 g product is obtained, i.e. a carboxyl perfluoropolyether compound (M2): $CF_3(OCF_2CF_2)_p(OCF_2)_q OCF_2CH_2OCH_2COOH$.

M2, M4, and M6 obtained from Synthesis Examples can react with an aminosilane coupling agent to further synthesize a perfluoropolyether-based silane compound, and can further subject to the following reactions, such as reacting with an acyl halogenation agent to produce an acylhalide $CF_3(OCF_2CF_2)_p(OCF_2)_q OCF_2CH_2OCH_2COL$ (wherein L is chlorine, bromine, or iodine); condensing with a carboxylate to produce an anhydride $CF_3(OCF_2CF_2)_p(OCF_2)_q OCF_2CH_2OCH_2COOCOR$; condensing with an alcohol to produce an ester $CF_3(OCF_2CF_2)_p(OCF_2)_q OCF_2CH_2OCH_2COOR$; reacting with an amine to produce an amide $CF_3(OCF_2CF_2)_p(OCF_2)_q OCF_2CH_2OCH_2CON$, and a primary amide can further be dehydrated to be prepared into a nitrile, obtaining $CF_3(OCF_2CF_2)_p(OCF_2)_q OCF_2CH_2OCH_2CN$.

Application Example 1

M2 obtained from Synthesis Examples 1 and 4 can be used to perform further reactions according to the following steps to synthesize a perfluoropolyether group containing silane compound A1: $CF_3(OCF_2CF_2)_p(OCF_2)_qOCF_2CH_2OCH_2CON[(CH_2CH_2CH_2Si(OCH_3)_3]_2$.

9.0 g carboxyl perfluoropolyether compound (M2) obtained in step 2 dissolved in 15 mL 1,3-bis(trifluoromethyl) benzene, 0.3 mL oxalyl chloride, are added into a 100 mL four-neck round-bottom flask equipped with a drop funnel, a thermometer and a stirrer. 0.2 mL DMF dissolved in 5 mL 1,3-bis(trifluoromethyl) benzene is slowly added dropwise via the drop funnel, then warmed up to 50° C. and stirred for 4 hours. After being reduced to room temperature, the reaction mixture is slowly added dropwise into a 250-mL three-neck round-bottom flask with 5 mL 1,3-bis(trifluoromethyl) benzene, 4.2 mL diisopropyl ethylamine, 4 mL bis(3-trimethyloxy silyl propyl) amine, and stirred at room temperature for 5 hours. 40 mL perfluorohexane is added. The reaction mixture is extracted three times with 18 mL methanol. The fluorine phase is distilled under decompression to remove the volatile components, and a colorless to pale yellow product is obtained, i.e. the following perfluoropolyether-based silane compound with a terminal trimethoxylsilane (A1): $CF_3(OCF_2CF_2)_p(OCF_2)_qOCF_2CH_2OCH_2CON[(CH_2CH_2CH_2Si(OCH_3)_3]_2$.

By identification with a NMR spectrometer, the characteristic $^1H$ chemical shifts are shown in the table below

| Group structure | δ, ppm |
|---|---|
| —OCH$_2$— | 4.469 (s) |
| —CF$_2$CH$_2$— | 4.197~4.118 (q) |
| —Si(OCH$_3$)$_3$ | 3.658~3.636 (d) |
| —CH$_2$CH$_2$CH$_2$ Si(OCH$_3$)$_3$ | 3.477~3.262 (m) |
| —CH$_2$CH$_2$CH$_2$Si(OCH$_3$)$_3$ | 1.868~1.769 (m) |
| —CH$_2$CH$_2$CH$_2$Si(OCH$_3$)$_3$ | 0.745~0.669 (m) |

Application Example 2

M4 obtained from Synthesis Example 2 can be used, according to the following steps, to synthesize a perfluoropolyether group containing silane compound A2: $CF_3(OCF_2CF_2)_p(OCF_2)_qOCF_2CH_2OCH_2CON[(CH_2)_3Si(OCH_3)_3]_2$.

9.0 g carboxyl perfluoropolyether compound (M4) obtained in step 2 dissolved in 18 mL 1,3-bis(trifluoromethyl) benzene, 0.23 mL oxalyl chloride are added into a 100 mL four-neck round-bottom flask equipped with a drop funnel, a thermometer and a stirrer. 0.15 mL DMF dissolved in 5 mL 1,3-bis(trifluoromethyl) benzene is slowly added dropwise via the drop funnel, and then warmed up to 50° C. and stirred for 4 hours. After being reduced to room temperature, the reaction mixture is slowly added dropwise into a 250-mL three-neck round-bottom flask with 9 mL 1,3-bis(trifluoromethyl) benzene, 1.6 mL diisopropyl ethylamine, 2.9 mL bis(3-trimethyloxy silyl propyl) amine, and stirred at room temperature for 5 hours. 72 mL perfluorohexane is added. The reaction mixture is extracted three times with 43 mL methanol. The fluorine phase is distilled under decompression to remove the volatile components, and a colorless to pale yellow product is obtained, i.e. the following perfluoropolyether-based silane compound having a terminal trimethoxylsilane (A2): $CF_3(OCF_2CF_2)_p(OCF_2)_qOCF_2CH_2OCH_2CON[(CH_2)_3Si(OCH_3)_3]_2$.

By identification with a NMR spectrometer, the characteristic $^1H$ chemical shifts are shown in the table below.

| Group structure | δ, ppm |
|---|---|
| —OCH$_2$— | 4.468 (s) |
| —CF$_2$CH$_2$— | 4.177~4.117 (m) |
| —Si(OCH$_3$)$_3$ | 3.656~3.634 (d) |
| —CH$_2$CH$_2$CH$_2$ Si(OCH$_3$)$_3$ | 3.468~3.270 (m) |
| —CH$_2$CH$_2$CH$_2$Si(OCH$_3$)$_3$ | 1.851~1.771 (m) |
| —CH$_2$CH$_2$CH$_2$Si(OCH$_3$)$_3$ | 0.730~0.667 (m) |

Application Example 3

M6 obtained from Synthesis Example 3 can be used, according to the following steps, to synthesize a perfluoropolyether group containing silane compound A3: $CF_3(OCF_2CF_2)_p(OCF_2)_qOCF_2CH_2OCH_2C_6H_4CON[(CH_2)_3Si(OCH_3)_3]_2$.

2.0 g carboxyl perfluoropolyether compound (M6) dissolved in 6 mL 1,3-bis(trifluoromethyl) benzene, 70 μL oxalyl chloride and 40 μl DMF, are added into a 100 mL four-neck round-bottom flask equipped with a drop funnel, a thermometer and a stirrer, and then warmed up to 50° C. and stirred for 5 hours. After being reduced to room temperature, the reaction mixture slowly added dropwise into a 25 mL three-neck round-bottom flask with 2 mL 1,3-bis(trifluoromethyl) benzene, 0.72 mL triethylamine, 0.85 mL bis(3-trimethyloxy silyl propyl) amine, and stirred at room temperature for 5 hours. 10 mL perfluorohexane is added. The reaction mixture is extracted five times with 4 mL methanol, and filtered with filtration membrane. After the volatile components is removed by distillation under decompression, 1.2 g of a colorless transparent product is obtained, i.e. the following perfluoropolyether-based silane compound having terminal trimethoxylsilane (A3): $CF_3(OCF_2CF_2)_p(OCF_2)_qOCF_2CH_2OCH_2C_6H_4CON[(CH_2)_3Si(OCH_3)_3]_2$.

By identification with a NMR spectrometer, the characteristic $^1H$ chemical shifts are shown in the table below

| Group structure | δ, ppm |
|---|---|
| —C$_6$H$_4$— | 7.512 (m) |
| —OCH$_2$— | 4.872 (s) |
| —CF$_2$CH$_2$— | 4.014 (m) |
| —Si(OCH$_3$)$_3$/—CH$_2$CH$_2$CH$_2$— | 3.683~3.416 (m) |
| —CH$_2$CH$_2$CH$_2$Si(OCH$_3$)$_3$ | 1.985~1.787 (m) |
| —CH$_2$CH$_2$CH$_2$Si(OCH$_3$)$_3$ | 0.891~0.509 (m) |

Application Example 4

M2 obtained from Synthesis Examples 1 and 4 can be used to perform further reactions according to the following steps to synthesize a perfluoropolyether group containing acyl chloride A4: $CF_3(OCF_2CF_2)_p(OCF_2)_qOCF_2CH_2OCH_2COCl$.

5.0 g carboxyl perfluoropolyether compound (M2) obtained in step 2 dissolved in 7.5 mL 1,3-bis(trifluoromethyl) benzene, and 0.17 mL oxalyl chloride are added into a 100 mL four-neck round-bottom flask equipped with a drop funnel, a thermometer and a stirrer. 0.15 mL DMF dissolved in 5 mL 1,3-bis(trifluoromethyl) benzene is slowly added dropwise via the drop funnel, then warmed up to 50° C. and stirred for 4 hours. A perfluoropolyetheryl acyl chloride A4: $CF_3(OCF_2CF_2)_p(OCF_2)_qOCF_2CH_2OCH_2COCl$, is obtained.

By identification with a NMR spectrometer, the characteristic $^1H$ chemical shifts are shown in the table below.

| Group structure | δ, ppm |
| --- | --- |
| —OCH$_2$— | 4.517(s) |
| —CF$_2$CH$_2$— | 4.016~3.956(q) |

By identification with a Fourier transform infrared spectrometer, the structural characteristic absorption peaks thereof are shown in the table below

| Group structure | λ, cm$^{-1}$ |
| --- | --- |
| —COCl | 1809(C=O stretch) |
| C—O/C—F | 1040~1335 (perfluoropolyether characteristic band) |

Application Example 5

M2 obtained from Synthesis Examples 1 and 4 can be used to perform further reactions according to the following steps to synthesize a perfluoropolyether group containing anhydride compound A5: CF$_3$(OCF$_2$CF$_2$)$_p$(OCF$_2$)$_q$OCF$_2$CH$_2$OCH$_2$COOCOCH$_3$.

3 mL 1,3-bis(trifluoromethyl) benzene, 0.41 mL triethylamine, and 0.55 mL acetyl chloride are added into a 100 mL four-neck round-bottom flask equipped with a drop funnel, a thermometer and a stirrer. 3 g carboxyl perfluoropolyether compound (M2) dissolved in 6 mL 1,3-bis(trifluoromethyl) benzene is slowly added dropwise via the drop funnel, and stirred for 4 hours at room temperature, then distilled under decompression to remove the volatile components, added 15 mL perfluorohexane. The reaction mixture is extracted with 6 mL acetonitrile for 3 times, then distilled under decompression to remove the volatile components, thus a canary yellow to yellow product is obtained, i.e., the following perfluoropolyether compound having a terminal anhydride (A5): CF$_3$(OCF$_2$CF$_2$)$_p$(OCF$_2$)$_q$OCF$_2$CH$_2$OCH$_2$COOCOCH$_3$.

By identification with a NMR spectrometer, the characteristic $^1$H chemical shifts are shown in the table below

| Group structure | δ, ppm |
| --- | --- |
| —CH$_2$COOCOCH$_3$ | 4.369(s) |
| —CF$_2$CH$_2$— | 4.064~4.000(m) |
| —CH$_2$COOCOCH$_3$ | 2.203(s) |

By identification with a Fourier transform infrared spectrometer, the structural characteristic absorption peaks thereof are shown in the table below

| Group structure | λ, cm$^{-1}$ |
| --- | --- |
| —COOCOCH$_3$ | 1841, 1778(C=O stretch) |
| C—O/C—F | 1040~1335 (perfluoropolyether characteristic band) |

Application Example 6

M2 synthetized from Synthesis Examples 1 and 4 can be used to perform further reactions according to the following steps to synthesize a perfluoropolyether group containing ester compound A6: CF$_3$(OCF$_2$CF$_2$)$_p$(OCF$_2$)$_q$OCF$_2$CH$_2$OCH$_2$COOCH$_3$.

5.0 g carboxyl perfluoropolyether compound (M2) obtained in step 2 dissolved in 7.5 mL 1,3-bis(trifluoromethyl) benzene, 0.17 mL oxalyl chloride are added into a 100 mL four-neck round-bottom flask equipped with a drop funnel, a thermometer and a stirrer. 0.15 mL DMF dissolved in 5 mL 1,3-bis(trifluoromethyl) benzene is slowly added dropwise via the drop funnel, then warmed up to 50° C. and stirred for 4 hours. After being reduced to room temperature, the reaction mixture is slowly added dropwise to a 100 mL three-neck round-bottom flask with 5 mL 1,3-bis(trifluoromethyl) benzene, 0.53 mL methanol, and 0.9 mL triethylamine therein, stirred at room temperature for 5 hours. 25 mL perfluorohexane is added, and extraction is performed for 3 times using 10 mL methanol, fluorine phase is distilled under decompression to remove the volatile components, and a colorless to light yellow product is obtained, i.e. the following perfluoropolyether based ester compound having a terminal methyl ester (A6): CF$_3$(OCF$_2$CF$_2$)$_p$(OCF$_2$)$_q$OCF$_2$CH$_2$OCH$_2$COOCH$_3$.

By identification with a NMR spectrometer, the characteristic $^1$H chemical shifts are shown in the table below.

| Group structure | δ, ppm |
| --- | --- |
| —CH$_2$COOCH$_3$ | 4.247(s) |
| —CF$_2$CH$_2$— | 4.072~4.010(q) |
| —CH$_2$COOCH$_3$ | 3.747(s) |

By identification with a Fourier transform infrared spectrometer, the structural characteristic absorption peaks thereof are shown in the table below

| Group structure | λ, cm$^{-1}$ |
| --- | --- |
| —COOCH$_3$ | 1765(C=O stretch) |
| C—O/C—F | 1040~1335 (perfluoropolyether characteristic band) |

Application Example 7

M2 synthetized from Synthesis Examples 1 and 4 can be used to perform further reactions according to the following steps to synthesize the perfluoropolyether group amide compound A7 having a terminal cyano: CF$_3$(OCF$_2$CF$_2$)$_p$(OCF$_2$)$_q$OCF$_2$CH$_2$OCH$_2$CONHC$_6$H$_4$CN.

5.0 g carboxyl perfluoropolyether compound (M2) obtained in step 2 dissolved in 7.5 mL 1,3-bis(trifluoromethyl) benzene, 0.17 mL oxalyl chloride are added into a 100 mL four-neck round-bottom flask equipped with a drop funnel, a thermometer and a stirrer, 0.15 mL DMF dissolved in 5 mL 1,3-bis(trifluoromethyl) benzene is slowly added dropwise via the drop funnel, then warmed up to 50° C. and stirred for 4 hours. After being reduced to room temperature, the reaction mixture is slowly added dropwise to a 100 mL three-neck round-bottom flask having 5 mL 1,3-bis(trifluoromethyl) benzene, 1.53 g 4-aminobenzonitrile, and 0.9 mL triethylamine therein, then warmed up to 50° C. and stirred for 5 hours. 25 mL perfluorohexane is added, and extraction is performed using 10 mL acetonitrile for 3 times. Fluorine phase is distilled under decompression to remove the volatile components, and a light yellow to yellow product, i.e. the following perfluoropolyether group amide compound A7 having a terminal cyano: CF$_3$(OCF$_2$CF$_2$)$_p$(OCF$_2$)$_q$OCF$_2$CH$_2$OCH$_2$CONHC$_6$H$_4$CN, is obtained.

By identification with a NMR spectrometer, the characteristic $^1$H chemical shifts are shown in the table below.

| Group structure | δ, ppm |
|---|---|
| —CH$_2$CONHC$_6$H$_4$CN | 8.482(s) |
| —CH$_2$CONHC$_4$H$_4$CN | 7.775~7.758(d), 7.684~7.667(d) |
| —CH$_2$CONHC$_6$H$_4$CN | 4.430(s) |
| —CF$_2$CH$_2$— | 4.299~4.226(m) |

By identification with a Fourier transform infrared spectrometer, the structural characteristic absorption peaks thereof are shown in the table below

| Group structure | λ, cm$^{-1}$ |
|---|---|
| —CONH— | 3400(N—H stretch) |
| —C$_6$H$_4$— | 2946(C═C—H stretch) |
| —CN | 2229(C═N stretch) |
| —CONH— | 1704(C═O stretch) |
| —C$_6$H$_4$— | 1605, 1592, 1525(C═C Skeletal) |
| C—O/C—F | 1040~1335 (perfluoropolyether characteristic band) |

Application Example 8

M2 obtained from Synthesis Examples 1 and 4 can be used to perform further reactions according to the following steps to synthesize a perfluoropolyether based geminal diphosphoric acid compound (A8): CF$_3$(OCF$_2$CF$_2$)$_p$(OCF$_2$)$_q$OCF$_2$CH$_2$OCH$_2$C(OH)[PO(OH)$_2$]$_2$.

Step 3:

5.0 g carboxyl perfluoropolyether compound (M2) obtained in step 2 dissolved in 7.5 mL 1,3-bis(trifluoromethyl) benzene, 0.17 mL oxalyl chloride, are added into a 100 mL four-neck round-bottom flask equipped with a drop funnel, a thermometer and a stirrer, 0.15 mL DMF dissolved in 5 mL 1,3-bis(trifluoromethyl) benzene is slowly added dropwise via the drop funnel, then warmed up to 50° C. and stirred for 4 hours, next distilled under decompression to remove the volatile components. 30 mL hydrofluoroether HFE-7200 is added to dissolve.

Step 4:

1.0 g phosphorous acid, 10 mL pyridine and 7.5 mL N,N-diisopropylethylamine are added into a 100 mL four-neck round-bottom flask equipped with a drop funnel, a thermometer and a stirrer, 5.3 mL trimethylchlorosilane dissolved in 15 mL tetrahydrofuran is slowly added dropwise via the drop funnel. A large amount of white loose white solid is produced immediately. After the addition in dropwise, the temperature returns to room temperature. The mix is warmed up and stirred under reflux for 3 hours, then reduced to room temperature. Acyl chloride HFE-7200 solution in step 3 is transferred to the drop funnel, then is slowly added dropwise into a round-bottom flask under stirring for 2 hours. 10 mL methanol is added into the round-bottom flask and stirred for another 1 hour at room temperature. Hydrochloric acid solution is added for acidification. After extraction of the fluorine phase with deionized water, distillation is performed under decompression to remove the volatile components, and a colorless or white solid product is obtained, i.e. the following perfluoropolyether based geminal diphosphoric acid compound (A8) having a terminal geminal diphosphoric acid: CF$_3$(OCF$_2$CF$_2$)$_p$(OCF$_2$)$_q$OCF$_2$CH$_2$OCH$_2$C(OH)[PO(OH)$_2$]$_2$.

By identification with a NMR spectrometer, the characteristic $^1$H chemical shifts are shown in the table below.

| Group structure | δ, ppm |
|---|---|
| —CH$_2$C(OH)[PO(OH)$_2$]$_2$ | 4.525~4.473(t) |
| —CF$_2$CH$_2$— | 4.345~4.267(q) |

By identification with a Fourier transform infrared spectrometer, the structural characteristic absorption peaks thereof are shown in the table below

| Group structure | λ, cm$^{-1}$ |
|---|---|
| —PO(OH)$_2$ | 2880(O—H stretch) |
| C—O/C—F | 1040~1335 (perfluoropolyether characteristic band) |

A4, A5 and A6 obtained in the above Synthesis Examples can be subjected to hydrolysis, alcoholysis and ammonolysis to produce the corresponding carboxylic acid, ester and amide derivatives and the like, which can be reduced to alcohols under the action of reducing agents such as lithium aluminum hydride, or reacted with organometallic reagents (such as Grignard reagent) to produce ketones, and via further reactions to produce alcohols. A7 obtained in the above Synthesis Examples can be subjected to hydrolysis and alcoholysis to produce the corresponding carboxylic acid, ester derivatives and the like, which can be reduced to the corresponding amines under the action of reducing agents such as lithium aluminum hydride. A8 has a phosphate group capable of chelating with metals, and can form a self-assembled monolayer film structure on the surface of metal or metal oxide. This technology is used in metal anti-corrosion, hydrophobic and oleophobic, lubricants, mold release agents, biosensing, electronic equipment interface controls and other fields.

As can be seen from the above Synthesis Examples and Application Examples, the carboxyl group containing perfluoropolyether-based compound of the present invention is an intermediate having a variety of applications, which is readily prepared, and can be further used to easily prepare a perfluoropolyether-based silane compound and the like.

The above Synthesis Examples and Application Examples are only for the purpose of illustrating the present invention, and are not limitations to the present invention. Ordinary technical persons in the relevant technical field may also make various changes and variation without departing from the scope of the present invention. Therefore, all equivalent technical solutions shall also belong to the scope disclosed in the invention.

The invention claimed is:

1. A carboxyl group containing perfluoropolyether compound, characterized by having the following general chemical formula (II):

wherein:

Rf is:

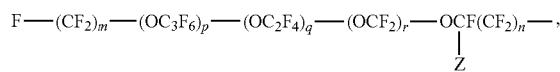

wherein p, q and r are each independently an integer of 1 or more and 200 or less, the sum of p, q and r is at least 1, the occurrence order of the respective repeating units in parentheses with the subscript p, q or r is arbitrary in the formula, m is an integer of 1 to 16, n is 0 or 1, Z represents a fluorine atom or a trifluoromethyl, or Rf represents $CF_3(OC_2F_4)_p(OCF_2)_qOCF_2$, wherein p, q are each independently an integer of 0 or more and 200 or less, the sum of p and q is at least 1, the occurrence order of the respective repeating units in parentheses with the subscript p, q is arbitrary in the formula; and X represents a divalent organic group.

2. The carboxyl group containing perfluoropolyether compound according to claim 1, wherein X represents $C_{1-6}$ alkylene group, —$CH_2C_6H_4$—, or —$CH_2C_6H_4$— with a substituent on the benzene ring.

3. The carboxyl group containing perfluoropolyether compound according to claim 1, wherein X is selected from a group consisting of —$CH_2$—, —$CH(CH_3)$—, —$(CH_2)_2$—, —$(CH_2)_3$—, —$(CH_2)_4$—, —$(CH_2)_6$— and —$CH_2C_6H_4$—.

4. The carboxyl group containing perfluoropolyether compound according to claim 1, wherein a number average molecular weight of the carboxyl group containing perfluoropolyether compound is 500-10,000.

5. A method for preparing a carboxyl group containing perfluoropolyether compound, the method comprising:

a) reacting a compound of the formula Rf—$CH_2OH$ with a first base in the presence of a solvent, then reacting with a compound of the formula L-X-G to perform a nucleophilic substitution, thus obtaining a perfluoropolyether compound of formula Rf—$CH_2$—O—X-G:

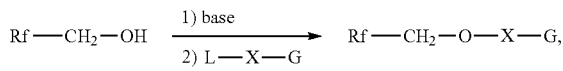

wherein:
Rf is:

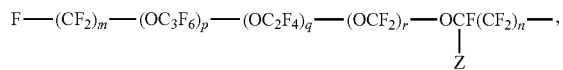

wherein p, q and r are each independently an integer of 1 or more and 200 or less, the sum of p, q and r is at least 1, the occurrence order of the respective repeating units in parentheses with the subscript p, q or r is arbitrary in the formula, m is an integer of 1 to 16, n is 0 or 1, Z represents a fluorine atom or a trifluoromethyl, or Rf represents $CF_3(OC_2F_4)_p(OCF_2)_qOCF_2$, wherein p, q are each independently an integer of 0 or more and 200 or less, the sum of p and q is at least 1, the occurrence order of the respective repeating units in parentheses with the subscript p, q is arbitrary in the formula;

L represents a leaving group or atom where a nucleophilic substitution reaction can occur;

G represents a group that can be hydrolyzed into a carboxylic acid; and

X represents a divalent organic group; and then b) hydrolyzing the compound of formula Rf—$CH_2$—O—X-G in the presence of a second base, and acidifying with an acid, to obtain a perfluoropolyether compound of formula Rf—$CH_2$—O—X—COOH:

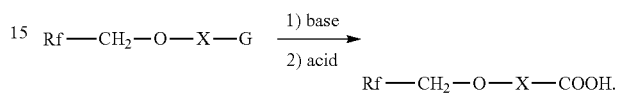

6. The method according to claim 5, wherein the first base is at least one selected from the group consisting of LiOH, NaOH, KOH, $K_2CO_3$, $Na_2CO_3$, $Cs_2CO_3$, NaH, t-BuOK, DIPEA, DBU, and 1,1,3,3-tetramethylguanidine.

7. The method according to claim 5, wherein L is a chlorine atom, a bromine atom, or an iodine atom.

8. The method according to claim 5, wherein G is an ester group, a nitrile group, an amide group, or a substituted amide group.

9. The method according to claim 5, wherein X is selected from the group consisting of —$CH_2$—, —$CH(CH_3)$—, —$(CH_2)_2$—, —$(CH_2)_3$—, —$(CH_2)_4$—, —$(CH_2)_6$— and —$CH_2C_6H_4$—.

10. The method according to claim 5, wherein that the solvent is a fluorinated solvent.

11. The method according to claim 5, wherein the second base is at least one selected from the group consisting of sodium hydroxide, potassium hydroxide, lithium hydroxide and cesium hydroxide.

12. The method according to claim 5, wherein the acid is an inorganic acid.

13. The method according to claim 5, wherein the acid is at least one of hydrochloric acid, sulfuric acid, or nitric acid.

14. A method for preparing a perfluoropolyether group containing silane compound, wherein the carboxyl group containing perfluoropolyether compound according to claim 1 an intermediate.

15. A method for treating a surface, the method comprising applying a surface treatment agent including the perfluoropolyether group containing silane compound produced by the method of claim 14 the surface.

16. The method of claim 15, wherein the surface treatment agent is a metal anti-corrosion agent, a hydrophobic agent, an oleophobic agent, a lubricant, a mold release agent, a biosensing agent, or an electronic equipment interface control agent.

* * * * *

UNITED STATES PATENT AND TRADEMARK OFFICE
CERTIFICATE OF CORRECTION

| | |
|---|---|
| PATENT NO. | : 12,037,352 B2 |
| APPLICATION NO. | : 17/055964 |
| DATED | : July 16, 2024 |
| INVENTOR(S) | : Yi-Jing Chen et al. |

Page 1 of 1

It is certified that error appears in the above-identified patent and that said Letters Patent is hereby corrected as shown below:

In the Claims

Column 20, Claim 14, Lines 45-46:
"according to claim 1 an intermediate."
Should read:
--according to claim 1 is an intermediate--.

Column 20, Claim 15, Line 50:
"by the method of claim 14 the surface."
Should read:
--by the method of claim 14 to the surface.--.

Signed and Sealed this
Seventeenth Day of September, 2024

Katherine Kelly Vidal
*Director of the United States Patent and Trademark Office*